(12) United States Patent
Arndt

(10) Patent No.: US 6,298,805 B1
(45) Date of Patent: Oct. 9, 2001

(54) FINGERPRINT INK DISPENSING APPARATUS

(75) Inventor: Douglas C. Arndt, Ventura, CA (US)

(73) Assignee: Identicator, Inc., El Segundo, CA (US)

( * ) Notice: Subject to any disclaimer, the term of this patent is extended or adjusted under 35 U.S.C. 154(b) by 0 days.

(21) Appl. No.: 09/543,798

(22) Filed: Apr. 6, 2000

(51) Int. Cl.$^7$ .................................................. B41K 1/00
(52) U.S. Cl. .................................................. 118/31.5; 427/1
(58) Field of Search ................................. 118/31.5, 264; 427/1; 283/68, 69; 382/124

(56) References Cited

U.S. PATENT DOCUMENTS

| | | |
|---|---|---|
| 2,746,192 * | 5/1956 | Norton ........................................ 41/4 |
| 3,898,360 | 8/1975 | Neumann et al. . |
| 3,971,335 | 7/1976 | Curtis et al. . |
| 4,553,837 | 11/1985 | Marcus . |
| 5,067,749 | 11/1991 | Land . |
| 5,395,444 | 3/1995 | Arndt . |
| 5,601,867 | 2/1997 | Riedl et al. . |
| 5,737,071 * | 4/1998 | Arndt ........................................ 356/71 |
| 5,811,366 | 9/1998 | Chikami . |
| 5,919,292 | 7/1999 | Arndt . |

\* cited by examiner

Primary Examiner—John S. Hilten
Assistant Examiner—Kevin D. Williams
(74) Attorney, Agent, or Firm—Harold L. Jackson

(57) ABSTRACT

A fingerprint ink pad arrangement, for use in taking rolled fingerprints, includes an ink reservoir formed of a porous material positioned against the inner wall of a cup shaped housing with a tubular substantially noncompressible ink dispensing substrate formed, for example, of a ceramic or plastic, positioned adjacent the ink reservoir so that ink flowing from the reservoir travels through the substrate to the fingerprint area.

16 Claims, 1 Drawing Sheet

FINGERPRINT INK DISPENSING APPARATUS

FIELD OF THE INVENTION

The present invention relates to fingerprint ink dispensing apparatus and more particularly to a fingerprint pad arrangement which more readily transfers the ink over an arcuate section of the finger to be printed requiring minimal or no rotation of the finger.

BACKGROUND OF THE INVENTION

Conventional ink, either of the carbon pigment based or of the chemical reagent nonstaining type, is applied to the fingers of a person to be fingerprinted and the fingers are then pressed against a recording medium such as a fingerprint card. The ink is generally transferred to the finger from a flat surface which may be in the form of a glass plate or a pad impregnated with the ink. To provide a recorded image of the entire print area it is first necessary to roll the fingers, nail to nail, across the flat inking surface and then roll the fingers over the designated areas on the card. It is often difficult to maintain the same finger to inking surface pressure during the rolling motion resulting in an uneven coating of ink on the finger. The uneven coating is then transferred to the card resulting in a less than optimum print.

In addition to the uneven coating problem it may be difficult to roll the fingers over a flat inking surface especially where rolling the finger is difficult, such as where the person is deceased or has disabling arthritis.

One attempt at solving the above problem is disclosed in U.S. Pat. No. 3,971,335 ("'335 patent"). This patent teaches the use of a compressible roller arrangement in which ink from a reservoir is transferred to the surface of the inking roller via an ink transfer drum. The transfer drum is driven by an electric motor. The '335 arrangement is not only complex and expensive to manufacture (and maintain) but probably will not solve the problem of providing a uniform coating of ink on the finger. Uneven compression of the inking roller around the finger will result in an uneven distribution of ink. Ink transferred from a non-compressible surface generally provides higher quality prints.

There is a need for a simple and reliable fingerprint ink dispensing apparatus for applying ink to the finger in preparation for the taking of rolled fingerprints.

SUMMARY OF THE INVENTION

A fingerprint ink dispensing apparatus for applying ink to a person's finger, in accordance with the present invention, includes a housing having a tubular inner wall with an open end. An ink reservoir in the form of a liquid absorbing medium, such as felt or the like, is positioned adjacent the inner wall of the housing. A substantially non-compressible hollow cylindrical ink metering substrate, made for example of porous ceramic or plastic, is positioned within the housing in intimate contact with the reservoir so that ink flowing from the reservoir travels through the substrate and onto the person's finger. The substrate has an inner diameter sufficient to accommodate the person's finger and a curvature approximating a major portion of the fingerprint area, i.e., nail to nail.

The present invention both as it's construction and features may best be understood by reference to the following description taken in conjunction with the accompanying drawing wherein like components are identified with the same reference numerals.

DESCRIPTION OF THE PREFERRED EMBODIMENT

Figure 1:
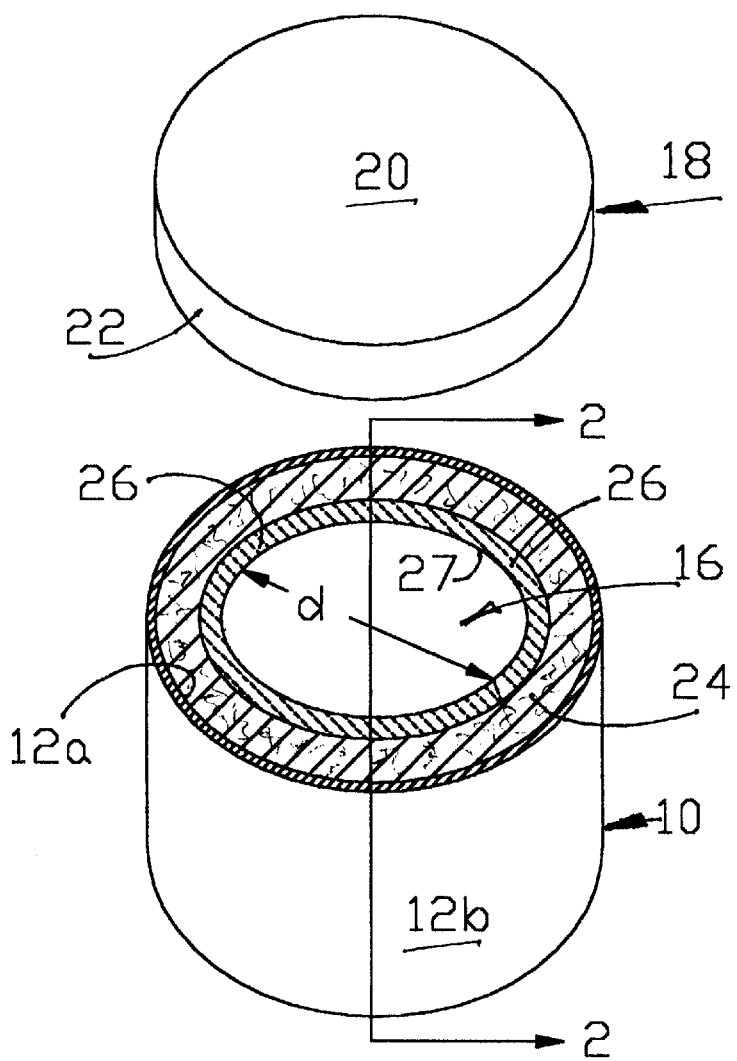
FIG. 1 is a perspective view of a fingerprint ink dispensing apparatus in the form of a tubular reservoir/metering pad with a closure cap in accordance with the present invention.
Figure 2:
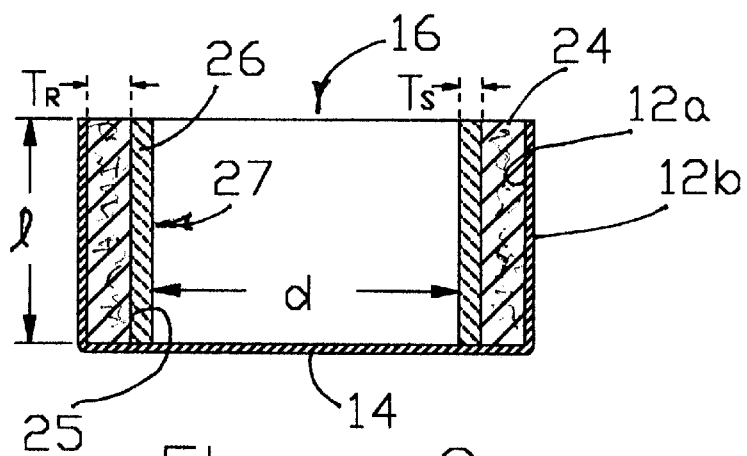
FIG. 2 is a cross-sectional view of the pad arrangement of FIG. 1 taken along lines 2—2 showing the placement of the ink reservoir and porous metering pad.

Referring now to the drawing and to FIGS. 1 and 2 thereof, a fingerprint ink dispensing apparatus, in accordance with the present invention, comprises a housing 10, preferably in the form of an open cylindrical container (or cup) having an inner cylindrical wall 12a, an outer peripheral wall 12b, a bottom wall 14, and an open top end 16. A closure cap 18 with a top wall 20 and peripheral downwardly extending lip 22 is arranged to close the open end of the housing 10 with the lip 22 snugly fitting around the upper portion of the outer peripheral wall 12b to inhibit the egress of fluid within the container to the atmosphere and inhibit the accumulation of dust on the ink dispensing substrate to be described. The housing is open at the top, as pointed out above, to provide access for a person's finger to an ink dispensing substrate or metering pad 26.

An ink reservoir 24, in the form of a tubular pad or structure of resilient foam, sponge or other porous material having interconnected interstitial spaces wherein the volume of the void within the structure is relatively large. A preferred reservoir 24 comprises a tubular felt pad. Alternatively, the reservoir 24 may comprise a ceramic or plastic material having a high porosity (e.g., 50% to 75% with an average pore size in the neighborhood of about 10–100 microns in diameter). The ink pad 24 has a cylindrical inner wall 25 which forms, with the bottom wall of the housing, a blind bore, for receiving the ink metering substrate or pad 26 to be described.

The metering pad 26 may be made of any suitable material such as a conventional ceramic containing silicon and metal oxides or a high density polyethylene plastic capable of metering an appropriate amount of ink to the fingerprint area.

The pad 26 is in the form of a tube 26 and is positioned within the housing, in intimate contact with the outer surface of the reservoir 24 so that liquid (i.e., ink) flowing from the reservoir must travel through the metering pad. The substrate or pad 26 serves to meter the ink dispersed by the reservoir to the fingerprint area of the person's finger to be printed. The metering pad preferably has a pore volume of 10 to 60 percent (10–60%) and a pore diameter distribution within the range of about 0.10 to 10.0 microns. The metering pad 26 should be substantially rigid and non-compressible in response to the pressure of a fingertip placed thereon for coating purposes. When the liquid composition is metered through a porous material with such specifications only the fine surfaces defining the fingerprint ridges are coated.

The use of pads which are compressible, such as typical stamp pads, have a tendency to cause overcoating of the finger, i.e., filling in the valleys along with coating ridges. Such overcoating generally results in flooded images having poor resolution. Also, such typical stamp pads do not deliver a consistent amount of liquid to the finger because as the liquid is depleted, the concentration within the substrate decreases with less liquid being delivered to the finger.

It should be noted that a substantially impermeable collar (not shown) may be secured between the top of the reservoir material and the edge of the metering pad to prevent liquid, i.e., ink, from migrating out of the upper edge or surface of the reservoir pad 24.

The inner cylindrical surface (i.e., elongated circular bore) 27 of the ink metering substrate or pad preferably has a diameter within the range of about ¾" to 1½" and most preferably about 1⅛". The length l, of the cylindrical bore may be of the order of 2 inches. The thickness, Ts, of the metering pad is preferably within the range of about 0.10" to 0.25" and most preferably about 0.15". The thickness, tr, of the ink reservoir pad is preferably within the range of about 1/10" to ¼" and most preferably about 1/16".

While a variety of fingerprint inks may be used in the reservoir/metering pad arrangement described above, several formulations of a preferred ink are described in my U.S. Pat. No. 5,919,292 ("'292 patent") which is assigned to the assignee of this application. The disclosure of the '292 patent is specifically incorporated herein by reference and made a part hereof.

While the invention has been described in connection with a preferred embodiment, it is not intended that the scope of the invention be limited to the particular embodiment. Modifications of the structure disclosed will become apparent to those skilled in the art without departing from the spirit and scope of the invention as defined by the appended claims.

What is claimed is:

1. Fingerprint ink dispensing apparatus for applying ink to a person's finger, a print of which is to be taken comprising:
   a cup-shaped housing having a tubular peripheral wall, a closed bottom end and an open top end;
   an ink reservoir positioned within the housing adjacent the peripheral wall thereof; and
   a substantially non-compressible hollow ink dispensing substrate positioned within the housing and in intimate contact with the reservoir so that ink flowing from the reservoir travels through the substrate, the substrate having a curved inner surface for accommodating a person's finger.

2. The invention of claim 1 further including a cap for closing the open end of the housing.

3. The invention of claim 2 wherein the inner surface of the ink dispensing substrate is substantially cylindrical having a diameter d within a range of about 1¾" to 1½".

4. The invention of claim 3 wherein the ink dispensing substrate is annular in form with thickness ts within the range of about 0.10" to 0.25".

5. The invention of claim 4 wherein the ink reservoir is annular in form with a thickness tr within the range of about 0.10" to 0.25".

6. The invention of claim 1 wherein the substrate has a pore volume within a range of about 10 to 60% and a pore diameter distribution within the range of about 0.10 to 10.0 microns.

7. The invention of claim 6 wherein the substrate is made of ceramic.

8. The invention of claim 6 wherein the substrate is made of plastic.

9. The invention of claim 8 wherein the plastic is a high density polyethylene.

10. A fingerprint ink pad arrangement comprising:
    a cup-shaped housing having a top open end, an elongated opening and a bottom end;
    a tubular wall extending along the elongated opening between the top end and the bottom end;
    an ink reservoir positioned within the elongated opening and adjacent the tubular wall in the housing; and
    a substantially non-compressible hollow ink dispensing substrate positioned within the housing and in intimate contact with the reservoir so that ink flows from the substrate which defines a cylindrical bore for accommodating a fingerprint area of a person's finger.

11. The invention of claim 10 wherein the ink reservoir and the substrate are in tubular form.

12. The invention of claim 11 wherein the ink reservoir comprises a porous material having interconnected interstitial spaces.

13. The invention of claim 12 wherein the porous material of the ink reservoir comprises a felt pad.

14. The invention of claim 12 wherein the ink dispensing substrate is made of ceramic.

15. The invention of claim 12 wherein the ink dispensing substrate is made of plastic.

16. A fingerprint ink pad comprising:
    a cup-shaped housing with an open top and a cylindrical blind bore;
    a tubular ink reservoir having an inner wall positioned within the blind bore, the ink reservoir containing an ink suitable for coating a person's finger to be fingerprinted; and
    a tubular metering pad positioned within the housing in intimate contact with the inner wall of the ink reservoir, the metering pad being substantially rigid and non-compressible in response to a pressure of a fingertip being placed thereon and having a porosity suitable for transferring a measured amount of ink to the fingertip.

* * * * *

UNITED STATES PATENT AND TRADEMARK OFFICE
CERTIFICATE OF CORRECTION

PATENT NO. : 6,298,805 B1
DATED : October 9, 2001
INVENTOR(S) : Arndt

It is certified that error appears in the above-identified patent and that said Letters Patent is hereby corrected as shown below:

<u>Column 3,</u>
Line 8, after "diameter" insert -- d --.
Line 9, "length l" should read -- length $\ell$ --.
Line 47, "13/4" should read -- 3/4" --.

Signed and Sealed this

Ninth Day of April, 2002

Attest:

JAMES E. ROGAN
*Attesting Officer*     *Director of the United States Patent and Trademark Office*